US006760104B2

(12) United States Patent
Gomelskiy

(10) Patent No.: US 6,760,104 B2
(45) Date of Patent: Jul. 6, 2004

(54) APPARATUS, METHOD, AND SYSTEM FOR ANALYZING SAMPLES USING TRIBOLUMINESCENT TECHNOLOGY

(76) Inventor: Grigoriy Gomelskiy, 85 Williamson Rd., Bergenfield, NJ (US) 07621

( * ) Notice: Subject to any disclaimer, the term of this patent is extended or adjusted under 35 U.S.C. 154(b) by 0 days.

(21) Appl. No.: 09/910,036

(22) Filed: Jul. 20, 2001

(65) Prior Publication Data

US 2003/0016351 A1 Jan. 23, 2003

(51) Int. Cl.[7] .................................................. G01J 3/30
(52) U.S. Cl. ....................................... 356/311; 356/326
(58) Field of Search ................................ 356/311, 317, 356/319, 326, 338, 328, 331; 250/306, 307

(56) References Cited

U.S. PATENT DOCUMENTS

| | | | | |
|---|---|---|---|---|
| 4,076,420 A | * | 2/1978 | De Maeyer et al. | 356/246 |
| 5,408,326 A | * | 4/1995 | Wang | 250/576 |
| 5,498,545 A | * | 3/1996 | Vestal | 250/288 |
| 5,998,146 A | | 12/1999 | Latva | |

FOREIGN PATENT DOCUMENTS

| | | | | |
|---|---|---|---|---|
| DE | 3240018 | | 5/1984 | |
| GB | 2 188 437 A | * | 9/1987 | G01N/7/14 |

OTHER PUBLICATIONS

V.E. Orel et al., "Physical and Engineering Principles in Study of Mechanically–Induced Emission of Blood," Biomedical Engineering. vol. 128, No. 6, 1994, pp. 335–337, Plenum Plublishing Corp.

Valerij E. Orel, "Physical Dosimetry and Biological Indicators of Carcinogenic Risk in a Cohort of Persons Exposed to Unhealthy Ecological Factors Following the Chernobyl Nuclear Power Plant Accident," Archives of Environmental Health, Nov. 1998 (downloaded from the Internet at www.findarticles.com/cf__ofm0907/6__53/53521638/print.jhtml on Jun. 8, 2001).

Valerij E. Orel "Light Emission During Activation of DNA" pp. 173–177. Date and place of publication unknown.

* cited by examiner

*Primary Examiner*—Euncha Cherry
(74) *Attorney, Agent, or Firm*—Goodwin Procter LLP

(57) ABSTRACT

An apparatus, method, and system are disclosed to analyze samples materials using triboluminescent technology. A mechanical activation knot is provided that comprises an optical window, a membrane, and a device that supplies a constant pressure of gas on the zone of activation. A sample is placed between the membrane and the optical window. The optical window is rotated along its z-axis. The friction between the sample and the optical window generates triboluminescence and associated optical emissions. Optical emissions may be distributed on the spectrum by a spectrograph, a monochromator, or a collection of filters, and then fixed by the charge coupled device, a photodiode, or a photomultiplier tube. Then, the results (data) are incorporated into different mathematical algorithms or programs with the help of computers or other computation technologies. The final results (the output) may be compared among themselves or with reference data stored in a computer's memory.

22 Claims, 4 Drawing Sheets

Mechanical Activation Knot (10)
F Pressure
Membrane (12)
Sample (13)
Optical Window (11)
hv
Device for spectrum division of light (Spectrograph) (20)
Detector Controller (40)
Detector for registration of optical emissions (CCD Head) (30)
Portable Computer (50)

Series1
Intensity
1150
950
750
550
350
150
-50
0
100
200
300
400
500
600
700
800
900
Spectrum nm

APPARATUS, METHOD, AND SYSTEM FOR ANALYZING SAMPLES USING TRIBOLUMINESCENT TECHNOLOGY

RELATED UNITED STATES APPLICATIONS/ CLAIM OF PRIORITY

Not applicable.

FIELD OF THE INVENTION

The present invention relates to an apparatus, method, and system for analyzing and identifying samples using triboluminescent technology.

BACKGROUND OF THE INVENTION

People have long detected the emission of light and other electromagnetic emissions in the process of applying mechanical stimulation, such as rubbing, deformation, scratching, striking, and fracture. This phenomenon is broadly known as mechanoemission and, in the case of light, has been observed for centuries and has several forms: triboluminescence (luminescence due to friction), mechanoluminescence (luminescence due to deformation of a material), and fractoluminescence (luminescence generated by fracturing a material). This mechanical stimulation may also generate electricity, also known as triboelectricity. The mechanoemission, in addition to an increase in temperature during the mechanical stimulation, emits optical and radio wave diapason of electromagnetic waves which conveys information about the material under investigation and can be recorded for analysis.

Presently, scientists from many countries study the phenomenon of triboluminescence, and research funds in the amount of billions of dollars are allocated to that effort. Specifically in the United States, a lot of time and effort is dedicated to the study of triboluminescence in many universities across the country.

One of the most important challenges in this field of study for scientists around the world and in the United States is to find a method of mechanical activation that would enable one to detect optical emissions with such characteristics (intensity and duration) that would allow for practical applications of the method of triboluminescence. Currently, methods experimented within this field are only able to detect a signal with low intensity and insignificant duration in time (picoseconds or nanoseconds). Further, registration and recording of these low intensity, short duration signals requires very expensive equipment.

One attempt is a triboluminometer that has been developed in the former Soviet Union (the "Russian Triboluminometer") at the Kiev Research Institute of Oncology in Kiev, Ukraine. The Russian Triboluminometer consists of (i) a mechanical activation knot; (ii) an electrode; (iii) a filter panel and associated mounting hardware; and (iv) a photomultiplier. The mechanical activation knot comprises an electret probe in the shape of a cylinder. The electret probe is composed of polytetrafluoroethylene (i.e., Teflon). The electret probe rotates around a shaft, which is connected to a motor. In the process of this rotation, the electret probe rubs against a sample, which creates an electric charge. The probe continues to rotate and comes in contact the operating electrode, securely grounded. As a result of this contact, an optical beam is emitted. This optical beam is then detected by the photomultiplier tube. The optical emissions are spectrally divided by a filter and registered by a photomultiplier. The usefulness of the Russian Triboluminometer, however, is limited because it generates a relatively weak signal of low intensity and short duration and does not adequately address the aforementioned problems.

SUMMARY OF THE INVENTION

The present invention overcomes the aforementioned problems of the prior art by providing a more efficient solution. The prior art does not provide the advantages and capabilities existing in the present invention. The present invention is an improvement upon the prior art in many aspects, for example: (1) it allows one to adjust the speed of rotation of an optical window while the device is in operation, and the force with which a sample is pressed between the membrane and the rotating window depending on the characteristics of any given sample; (2) it allows for a higher limit of adjustable speed; (3) its optical window is more durable; (4) it is capable of detecting a signal of optical emissions at a much greater resolution for a longer duration; (5) it uses a membrane that provides an even distribution of force on all contact points of a sample; and (6) it ensures that the rotation and activation takes place only after a sample is firmly and completely pressed against the optical window, whereas in the prior art, a sample is being pressed to an electret probe as it is being rotated.

According to a first aspect of the present invention, an apparatus for analyzing samples using triboluminescent technology is provided. The apparatus comprises a mechanical activation knot that generates triboelectricity, wherein the mechanical activation knot comprises an optical window, a membrane, and a device that supplies a constant pressure of gas to a zone of activation. The apparatus further comprises a device for dividing the spectrum of optical emissions and a detector for registration of optical emissions. A detector controller amplifies and digitizes signals received by the detector. Digitized signals are sent to a portable computer to be stored and analyzed.

In a second aspect of the present invention, a method for analyzing samples using triboluminescent technology is provided. The method of the present invention comprises placing a sample between an optical window and a membrane of a mechanical activation knot; supplying a constant pressure of a gas on a zone located between the membrane and the optical window; rotating the optical window to generate triboluminescence, and resulting optical emissions, from the friction between the sample and the optical window; directing optical emissions through a device for dividing the spectrum of optical emissions; detecting the intensity of the optical emissions across the spectrum of the optical emissions; amplifying and digitizing the detected signals; and storing and analyzing the digitized signals.

In a third aspect of the present invention, a system for analyzing samples using triboluminescent technology is provided. The system comprising means for preparing a sample; means for creating optical emissions by generating friction between the sample and an optical window; means for dividing the spectrums of optical emissions; means for detecting optical emissions; means for amplifying and digitizing detected signals; and means for storing and analyzing the digitized signals.

In contrast to the prior art, some technical characteristics (such as the intensity, resolution and duration of the signal) of the present invention show an improvement of up to one million times. In addition, this instrument is relatively inexpensive, thereby hastening widespread adoption and permitting others to conduct research. The present invention may be used in any industry, science, medicine, space exploration, defense and military.

These and other aspects, features, and advantages of the present invention will become better understood with regard to the following description, claims, and accompanying drawings.

BRIEF DESCRIPTION OF THE DRAWINGS

Referring briefly to the drawings, embodiments of the present invention will be described with reference to the accompanying drawings in which.

DETAILED DESCRIPTION OF THE INVENTION

Figure 1:
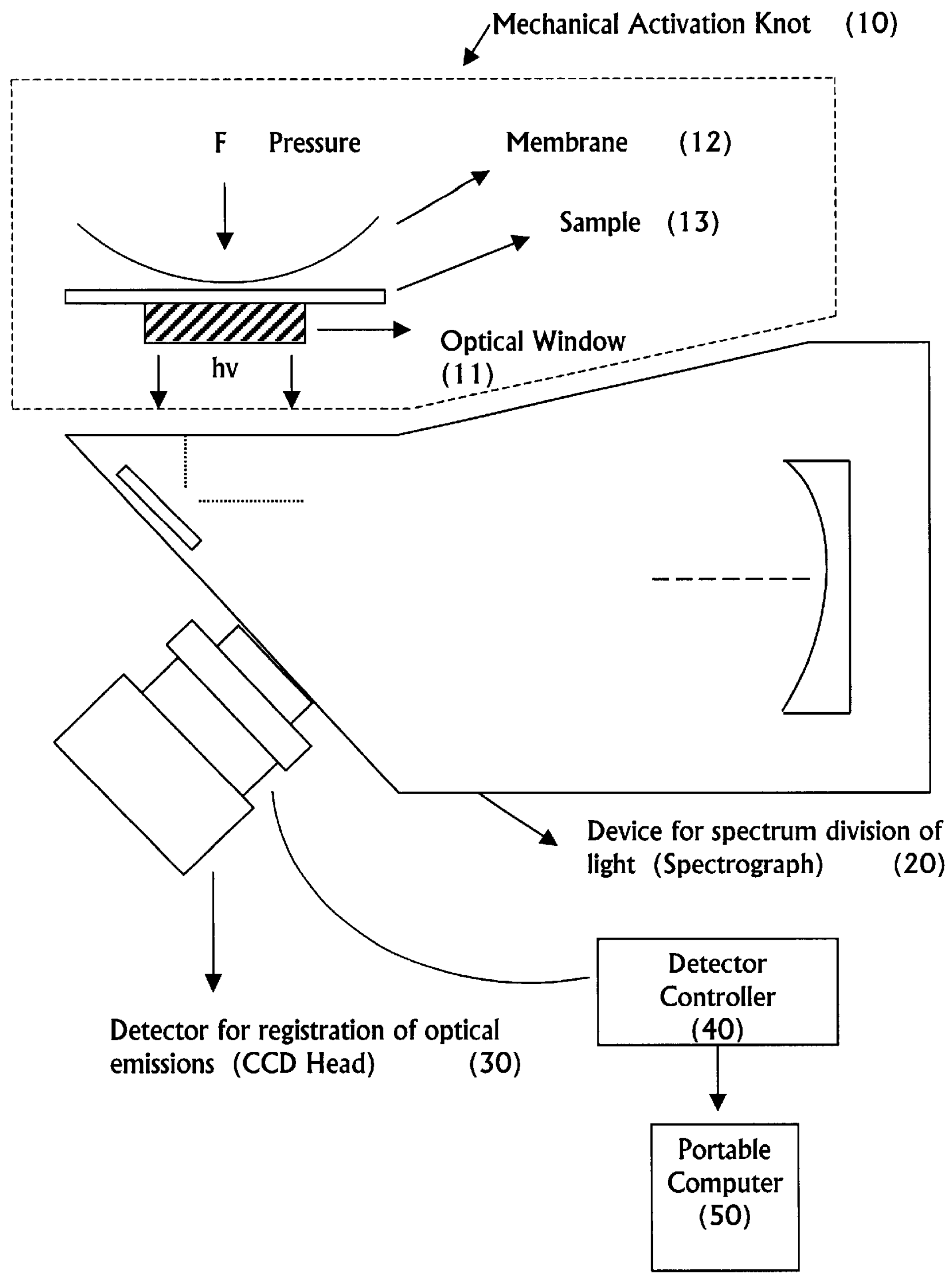
FIG. 1 depicts the hardware configuration of the present invention.
Figure 2:
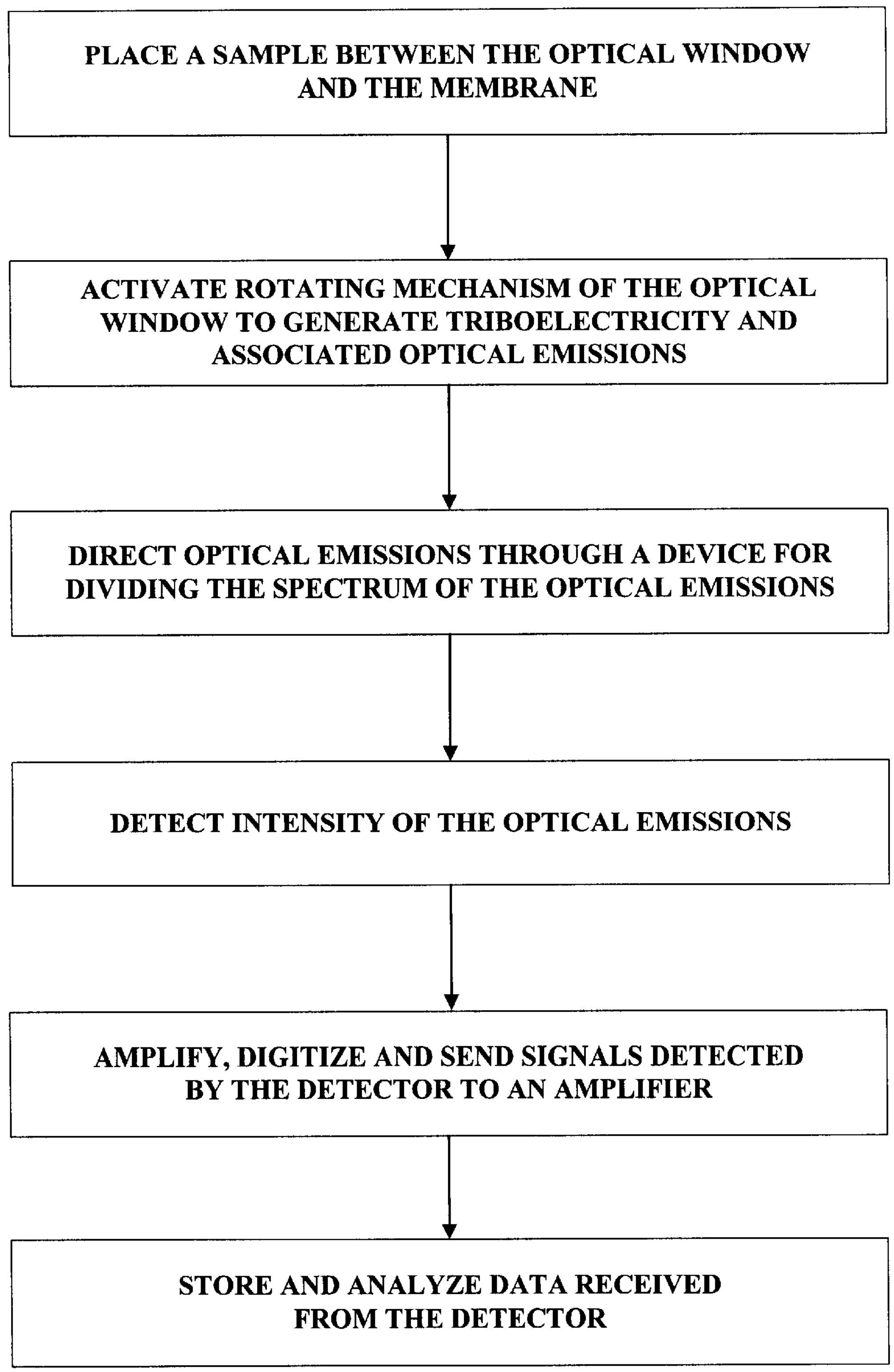
FIG. 2 depicts a flow chart that illustrates the steps related to the method or process of one aspect of the present invention.

Referring more specifically to the drawings, for illustrative purposes the present invention is embodied in the system configuration, method of operation, and article of manufacture or product generally shown in FIGS. 1–2. It will be appreciated that the system, method of operation, and article of manufacture may vary as to the details of its configuration and operation without departing from the basic concepts disclosed herein. The following detailed description is, therefore, not to be taken in a limiting sense.

The present invention can use used to analyze a number of materials and substances, including (i) liquids, such as water, alcohol, perfume, oil, petroleum and the like, in their pure form or with added ingredients, such as salt or sugar; (ii) condensed products of human breath; (iii) whole blood and its components (lymphocytes, lipoproteins, etc); (iv) tear, urine, saliva, sperm and their components in humans and animals; and (v) DNA. Following is (i) a discussion of sample preparation; (ii) a discussion of the instrument and its components; and (iii) a discussion of the operation of the instrument, including an example.

I. Sample Preparation

A biological sample in its liquid form is placed on a substrate (made out of paper, fabric, leather, cellulose, etc) by a pipette. Then, it is dried in an incubator, where certain temperature and humidity levels are set (typically, humidity levels are 40% to 45% and the temperature is around 37° Celsius). The length of time a sample stays in the incubator depends on the chemical composition of a sample and the goal of the experiment. There are several advantages of this type of sample preparation. First, it is relatively inexpensive because it does not require the use of pure chemical ingredients that are usually very expensive. Second, a sample is stored in a dried rather than liquid condition. The fact that a sample is stored in liquid form significantly prolongs storage time under reduced temperature conditions (a dried sample could be stored in a regular refrigerator for up to six month without impairing its chemical composition, whereas a liquid sample would oxidize under these storage conditions); and enables a convenient, easy, safe and inexpensive transportation of the sample without the need for sophisticated equipment (a sample can be shipped via mail in a plastic bag).

II. The Instrument and its Components

Referring to FIG. 1, one embodiment of the present invention is shown. The present invention comprises: (i) a mechanical activation knot (10); (ii) a device for division of the spectrum of optical emissions (20); (iii) a detector for registration of optical emissions (30); (iv) a detector controller (40); and (v) a computer (50). Each of these components are described in detail below.

The mechanical activation knot (10), comprises: (i) an optical window (11); (ii) a membrane (12); and (iii) a device that supplies to the zone of activation a constant pressure of a gas, such as oxygen or nitrogen. An optical window made of sapphire is connected to a device, via a shaft, that is capable of rotating the window, such as an electric motor (the shaft and electric motor are not illustrated in FIG. 1). After a sample (13) is placed against the optical window, the electric motor rotates the optical window to create mechanoemission. The mechanical activation knot (10) of the present invention is an improvement over the prior art because it has a higher limit of adjustable speed of activation, which allows for greater intensity of the optical emission.

In one embodiment of the present invention, single crystal sapphire is used as the material for the optical window (11). Sapphire windows are ideal for demanding applications, such as laser system, because of extreme hardness (second only to diamonds among crystals), high thermal conductivity, high dialectic constant and resistance to common chemical acids and alkalis. Because of the structural strength of sapphires, sapphire windows can be made much thinner than other common dialectic windows with improved transmittance, with transmissions ranging from 0.15–5.5 microns. Although other materials with good mechanical properties and transmission ranging from 180 to 1100 nanometers (nm) may be substituted for an optical window (11), such as fused silica, optical sapphire still has superior quality and characteristics for the purposes of the optical window (11). The use of sapphire glass for the optical window (11) is an improvement over the prior art's use of an electret probe. The significance of using sapphire material lies in its extreme hardness (second only to diamonds among crystals) and durability compared to a relatively soft material like Teflon. Using sapphire glass that is resistant to damage associated with friction ensures the accuracy of testing results.

The use of a sapphire glass optical window (11) also reduces the amount of signal loss compared to the prior art. In the prior art, a sample is pressed against an electret probe to generate optical emissions. There is a gap between the surface of the sample and a photomultiplier tube to accommodate a filter holder (for the photomultiplier), an electrode, and a shutter. This gap results in a significant loss in intensity of the signal (optical emission). To generate optical emissions, the present invention uses a sapphire window that is very thin due to extreme hardness of sapphire material. The sapphire window is located very close to the entrance slit of the spectrograph, which minimizes signal loss. It also eliminates the need to use lenses, fiber optics, mirrors, etc.

The membrane (12) serves to ensure that the same amount of pressure is consistently applied on every point of a sample (13) in pressing it onto an optical window (11). Maintaining constant pressure across a sample (13) is important to achieving accurate test results by ensuring that similar samples provide similar results on a consistent basis. If a constant, consistent pressure is not applied to the sample, the sample will come into contact with the optical window in a random manner. In one preferred embodiment of the present invention, the membrane (12) is composed of rubber. The present invention is not limited to a membrane (12) to perform this function. There are several alternative ways of applying pressure on a sample (13). However, no matter what means are used to apply pressure, there must be consistent pressure that ensures repeatability in detected characteristics.

The present invention is also an improvement over the prior art because it has a higher limit of adjustable force applied to the sample (13), which allows for greater intensity of the optical emission. Further, in the present invention the speed of rotation of the optical window and force applied may be adjusted and selected, through the use of an external mechanism such as a knob, depending on the goal of the experiment and sample tested. In the prior art, the speed and the force applied to a sample (13) cannot be adjusted through an external mechanism. The present invention could also be used with a still optical window with a rotating sample instead of a rotating optical window and a still sample.

In one embodiment of the present invention, high purity nitrogen is supplied through a tube to a zone of activation, located between the optical window (11) and the sample (13), at a constant pressure, which ensures that the environment around the sample is stabilized.

Devices used for spectrum division of optical emissions (20) include a spectrograph, a monochromator, or filters. These devices collect, spectrally disperse optical emissions, and reimage the optical emissions as an output signal. The output signal is a series of monochromatic images corresponding to the wavelengths present in the light imaged at the entrance slit. One preferred embodiment of the present invention comprises a spectrograph (20) that presents a range of wavelengths at the exit focal plane for detection by a multi-channel detector or photographic film. The present invention is an improvement of the prior art's use of a panel of 26 interference light filters at wavelengths ranging from 252 to 649 nm, with a margin of 9 nm. In order to receive a fingerprint of any given sample in graph form, the prior art has to make 26 identical samples of the same substance and use 26 different filters, each of which recording a certain range of data. Then, the prior art connects these 26 discrete points of data to create a graph. One advantage of the present invention is that a spectrograph (20) and CCD head (30) are able to record all data at once and by using one sample. Thus, the present invention has the advantage of producing a more accurate result with higher resolution, as well as saving testing time by eliminating the need for running multiple sample tests. Although the use of filters is not excluded from the present invention, embodiments that do not use filters are an improvement over the prior art because there would be no need for additional parts that hold and change filters, which decreases the total size and weight of the apparatus.

Detectors for registration of optical emissions (30) include a charge coupled device (CCD), photodiode (PDA), or a photomultiplier (PMT). Any one of these detectors measures radiant intensity of each narrow bandwidth which is selected sequentially by the scanning the devices used for the spectrum division of optical emissions (20), such as a spectrograph or a monochromator. The detector (30) converts the radiation of the optical emission into an electric signal. This signal can be amplified and measured by a detector controller (40). The present invention's use of a spectrograph (20) and CCD head (30) combination makes it possible to receive a resolution that is up to 1000 times greater (depending on technical characteristics) than the resolution of the filter panel used by the prior art. There are many advantages of using CCD systems, as opposed to filters. CCD systems provide the advantages of (i) seeing the entire spectrum simultaneously; (ii) registering source fluctuations across the entire spectrum; (iii) allowing "real time" visual monitoring; (iv) allowing multiple sources and spatial studies because of a second dimension; (v) allowing for optimization of signal/noise through the use of binning and grouping of pixels; (v) limiting dark signals through the use of LN2 cooled CCDs; and (vi) improving quantum efficiency.

A detector controller (40) is used to control a CCD head, PDA, or PMT based on commands from a computer (50). The detector controller (40) supplies power, clocking signals, synchronization, and biases to a detector (CCD, PDA, or PMT). The detector controller (40) also amplifies and digitizes the signal as it is collected from the detector.

A computer (50) is used to store and process data, as well as display information, such as graphs, comparison charts and the like. The present invention's use in conjunction with a computer (50), a CCD Controller (40) and special software, is an improvement over the prior art because it makes it possible to alter the power, temperature control and timing signals to the detector head (30).

III. How the Instrument is Operated

Referring to FIG. 2, the process or flow chart for operating the instrument is shown. As shown in block 1, the initial step is to place a sample (13) between the optical window (11) and the membrane (12). As shown in block 2, after full pressure is applied on the sample (13) to the optical window (11), an electric motor rotates the optical window (11) about its z-axis. The friction created between the sample (13) and the optical window (11) creates triboelectricity, which triggers the activation process of mechanochemical free-radical reaction of the sample (13). During this process, in addition to temperature increase, there is the emission in the optical and radiowave diapason of the electromagnetic waves. Optical emissions are then detected as a result of mechanoemission.

In the present invention, the optical window (11) is not rotated until a sample (13) is fully pressed to the optical window (11). This is an improvement over the prior art where there is a continuous rotation of an electret probe. This difference is very important in achieving accurate test results. Typically, when samples are prepared, liquid biosamples (blood, saliva, tears, etc.) in the amount of 0.02–0.05 ml are applied by a pipette on the cellulose or cotton paper. Then, the paper is dried. In the prior art, the sample is pressed against the electret probe while the electret probe is rotating. This method of pressing the sample against the probe results in multiple points of contact that are random each time the sample comes in contact with the probe because a liquid sample somewhat deforms the shape of the paper while it dries. Thus, it is not possible to ensure repeatability in results each time similar samples are examined. In the present invention, there is no rotation of the optical window (11) until a completely dried sample (13) is pressed firmly between the optical window (11) and the membrane (12). The membrane (12) serves to ensure that each point of the sample (13) comes in contact with the optical window (11) in a uniform way. Only then will the optical window (11) begin to rotate, with the results being recorded. The advantage of present invention is that it ensures the accuracy of the results and repeatability in testing that was impossible to achieve using the prior art. Depending on the chemical composition of the sample and the objectives of the experiment, a certain temperature and humidity must be ensured when the present invention is in the operation.

As shown in block 3, optical emissions are directed through a device to divide the spectrum of optical emissions (20), such as a spectrograph, monochromator, or a filter. The optical emissions are then directed to a detector (30).

As shown in block 4, optical emissions are detected by a detector (30) such as a coupled charge device (CCD), a photodiode (PD), or a photomultiplier tube (PMT).

As shown in block 5, signals received by the detector (30) are amplified and digitized by a detector controller (40). The detector controller (40) sends the amplified and digitized signals (the "results") to a computer (50). As shown in block 6, the computer (50) stores the results in memory and analyzes the data. The results may be analyzed in a variety of ways, including: (i) comparison of peaks on a given graph; (ii) comparison of a graph with a reference graph; (iii) comparison of parts of a graph; (iv) comparison of detected results with reference results stored on computer memory; and (v) comparison of different points on a graph.

To clean the surface of the optical window (11) after its contact with the sample (13), it is necessary to do the following: (i) wipe the surface of the optical window (11) with a special wet tissue that is used for optical windows, or (ii) prepare a special tissue by putting a drop of an alcohol substance of 20–30% or lens cleaner on a piece of paper or fabric. To neutralize the static charge, it is necessary to do the following after each test: (i) insert a thin metal grounded sheet in place of a sample (13); and (ii) press this sheet between the optical window (11) and the rubber membrane (12) without rotating the optical window (11).

EXAMPLE

The following illustrates one embodiment of the present invention. A working prototype of the present invention is currently available. It comprises: (i) a mechanical activation knot comprising a very thin optical window (0.5 mm) (11) made out of single crystal sapphire; (ii) a Spectrograph CP-140, manufactured and supplied by the ISA Company (US); (iii) a Mini Thermoelectrically Cooled CCD Head, manufactured and supplied by the ISA Co.; (iv) a Spectrum One Controller, manufactured and supplied by the ISA Co.; and (v) a portable computer, manufactured and supplied by Compaq. The prototype has an adjustable speed of activation of up to 5000 RPM. In the prototype, the force applied to a sample (13) is done with a rubber membrane (12) and the force can be adjusted from 0.5 to 2000 mm of Mercury (Hg).

The prototype operates between a range of temperature of 18° to 40° Celsius. Depending on the chemical composition of the sample (13) and the objectives of the experiment, certain humidity must be ensured when the instrument is in the operation. The prototype operates between a range of humidity of 40% to 97% relative humidity (RH).

The prototype enables detection of optical emissions with intensity for up to 10 to the power of 12 quantums. The duration of signal registration is from 1 millisecond to 30 seconds depending on the object of the experiment and what is used as a sample (13).

Figure 3:
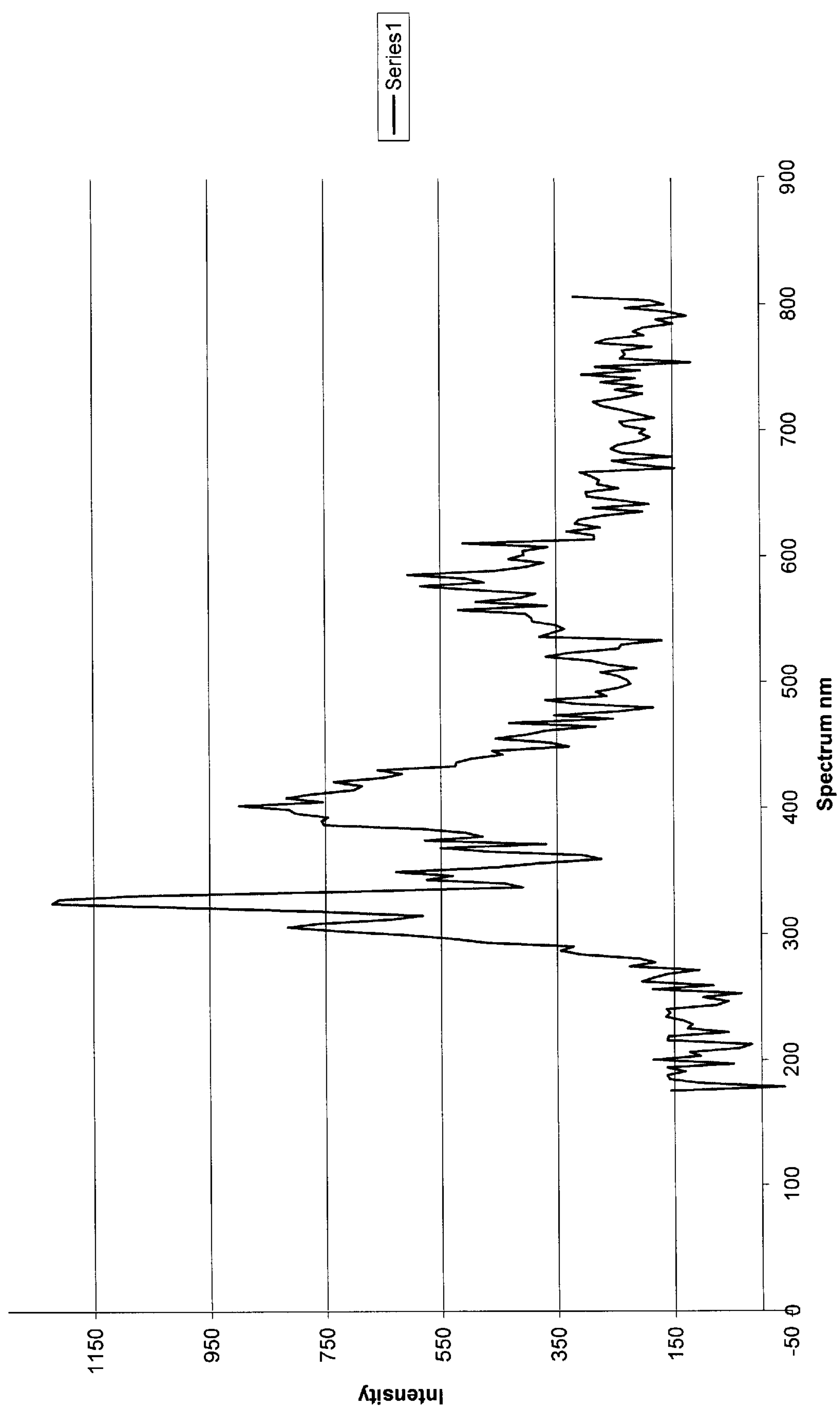
FIG. 3 depicts output of the present invention when inkjet paper is used as a sample material.
Figure 4:
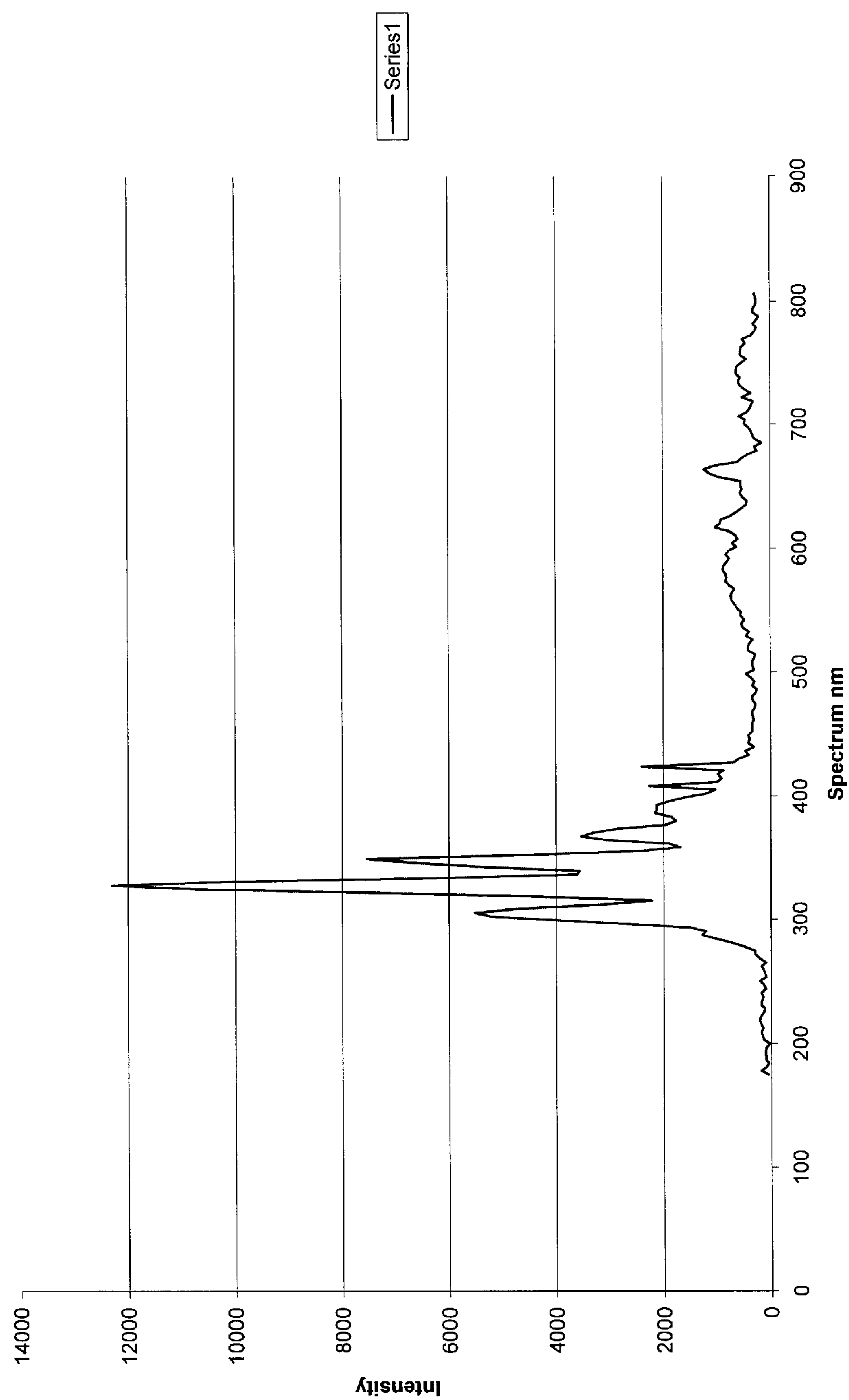
FIG. 4 depicts output of the present invention when 100 cotton fiber paper is used as a sample material.

FIGS. 3 and 4 illustrate the output of this prototype instrument when inkjet paper and 100% cotton fiber paper are used as samples respectively. FIGS. 3 and 4 demonstrate that the present invention is able to recognize the difference in composition of these samples.

Having now described an embodiment of the invention, it should be apparent to those skilled in the art that the foregoing is illustrative only and not limiting, having been presented by way of example only. All the features disclosed in this specification (including any accompanying claims, abstract, and drawings) may be replaced by alternative features serving the same purpose, and equivalents or similar purpose, unless expressly stated otherwise. Therefore, numerous other embodiments of the modifications thereof are contemplated as falling within the scope of the present invention as defined by the appended claims and equivalents thereto.

What is claimed is:

1. An apparatus for analyzing samples using triboluminescent technology comprising:

a mechanical activation knot that generates triboluminescence, wherein the mechanical activation knot is further comprised of an optical window, and a membrane;

a device for dividing the spectrum of optical emissions; and a detector for registration of the optical emissions.

2. The apparatus for analyzing samples using triboluminescent technology of claim 1, further comprising a detector controller.

3. The apparatus for analyzing samples using triboluminescent technology of claim 1 or 2, wherein the optical window is comprised of single crystal sapphire.

4. The apparatus for analyzing samples using triboluminescent technology of claim 1 or 2, wherein the optical window is composed of fused silica.

5. The apparatus for analyzing samples using triboluminescent technology of claim 1, wherein the device for dividing the spectrum of optical emissions is a spectrograph.

6. The apparatus for analyzing samples using triboluminescent technology of claim 1, wherein the device for dividing the spectrum of optical emissions is a monochromator.

7. The apparatus for analyzing samples using triboluminescent technology of claim 1, wherein the device for dividing the spectrum of optical emissions is a filter panel.

8. The apparatus for analyzing samples using triboluminescent technology of claim 1, wherein the detector is a charged coupling device.

9. The apparatus for analyzing samples using triboluminescent technology of claim 1, wherein the detector is a photodiode.

10. The apparatus for analyzing samples using triboluminescent technology of claim 1, wherein the detector is a photomultiplier tube.

11. A system for analyzing samples using triboluminescent technology comprising:

means for creating triboluminescence, and resulting optical emissions, by generating friction between a sample and an optical window;

means for dividing the spectrum of optical emissions; and means for detecting optical emissions.

12. The system for analyzing samples using triboluminescent technology of claim 11, further comprising means for amplifying and digitizing detected signals of optical emissions.

13. The system for analyzing samples using triboluminescent technology of claim 12, further comprising means for storing and analyzing the digitized signals.

14. The system for analyzing samples using triboluminescent technology of claim 11, 12, or 13, wherein the means for creating triboluminescence is a mechanical activation knot comprising an optical window composed of single crystal sapphire.

15. The system for analyzing samples using triboluminescent technology of claim 11, 12, or 13, wherein the means for creating triboluminescence is a mechanical activation knot comprising an optical window composed of fused silica.

16. The system for analyzing samples using triboluminescent technology of claim 11, wherein the means for dividing the spectrum of optical emissions is a spectrograph.

17. The system for analyzing samples using triboluminescent technology of claim 11, wherein the means for dividing the spectrum of optical emissions is a monochromator.

18. The system for analyzing samples using triboluminescent technology of claim 11, wherein the means for dividing the spectrum of optical emissions is a filter panel.

19. The system for analyzing samples using triboluminescent technology of claim 11, wherein the means for detecting optical emissions is a charge coupled device.

20. The system for analyzing samples using triboluminescent technology of claim 11, wherein the means for detecting optical emissions is a photodiode.

21. The system for analyzing samples using triboluminescent technology of claim 11, wherein the means for detecting optical emissions is a photomultiplier tube.

22. A method for analyzing samples using triboluminescent technology, the method comprising:

providing a system for analyzing samples using triboluminescent technology comprising:

- a mechanical activation knot that generates triboluminescence, wherein the mechanical activation knot is further comprised of an optical window, and a membrane;
- a device for dividing the spectrum of optical emissions; and
- a detector for registration of the optical emissions.

* * * * *